(12) United States Patent
Kugo et al.

(10) Patent No.: US 12,108,932 B2
(45) Date of Patent: Oct. 8, 2024

(54) VARIABLE-RIGIDITY DEVICE, CONTROL DEVICE, AND METHOD FOR CONTROLLING ACTUATOR

(71) Applicant: OLYMPUS CORPORATION, Tokyo (JP)

(72) Inventors: Tomoyuki Kugo, Matsudo (JP); Takeshi Takahashi, Hachioji (JP); Tomohiro Kitanaka, Higashimurayama (JP)

(73) Assignee: OLYMPUS CORPORATION, Tokyo (JP)

( * ) Notice: Subject to any disclaimer, the term of this patent is extended or adjusted under 35 U.S.C. 154(b) by 642 days.

(21) Appl. No.: 17/408,935

(22) Filed: Aug. 23, 2021

(65) Prior Publication Data

US 2021/0378485 A1 Dec. 9, 2021

Related U.S. Application Data

(63) Continuation of application No. PCT/JP2019/007684, filed on Feb. 27, 2019.

(51) Int. Cl.
  *F16C 1/12* (2006.01)
  *A61B 1/00* (2006.01)
  (Continued)

(52) U.S. Cl.
  CPC ...... *A61B 1/00078* (2013.01); *A61B 1/00006* (2013.01); *A61B 1/0052* (2013.01);
  (Continued)

(58) Field of Classification Search
  CPC .. F16C 1/12; F16C 1/20; B25J 19/068; A61B 1/00006; A61B 1/00078; A61B 1/0051; A61B 1/0052; A61B 1/0057
  See application file for complete search history.

(56) References Cited

U.S. PATENT DOCUMENTS 10,369,328 B2 * 8/2019 Tsai ................. A61M 25/0009
11,117,272 B2 * 9/2021 Takahashi ................ A61B 1/00
(Continued)

FOREIGN PATENT DOCUMENTS

GB          2584549 A  * 12/2020  .......... A61B 1/0051
JP       2002-027759 A    1/2002
(Continued)

OTHER PUBLICATIONS

Machine translation of WO 2017/191686 A1 obtained on May 31, 2024.*

(Continued)

*Primary Examiner* — Adam D Rogers
(74) *Attorney, Agent, or Firm* — Scully, Scott, Murphy & Presser, P.C.

(57) ABSTRACT

A variable-rigidity device includes a tubular member including a plurality of high-rigidity portions and low-rigidity portions arranged along a longitudinal axis, a core member arranged on an inner side of the tubular member and including a plurality of high-rigidity core portions and low-rigidity core portions; and an actuator configured to relatively move the core member with respect to the tubular member, in which the actuator is configured to cause a first force to repeatedly fluctuate with a passage of time, the first force causing the core member to relatively move with respect to the tubular member in an axial direction along the longitudinal axis.

11 Claims, 7 Drawing Sheets

(51) Int. Cl.
*A61B 1/005* (2006.01)
*F16C 1/20* (2006.01)

(52) U.S. Cl.
CPC .............. *A61B 1/0057* (2013.01); *F16C 1/12* (2013.01); *F16C 1/20* (2013.01); *A61B 1/0051* (2013.01); *A61B 1/0055* (2013.01)

(56) References Cited

U.S. PATENT DOCUMENTS

| | | | | |
|---|---|---|---|---|
| 11,259,690 | B2* | 3/2022 | Okita | A61B 1/0055 |
| 11,389,052 | B2* | 7/2022 | Okita | A61B 1/0058 |
| 11,399,704 | B2* | 8/2022 | Takahashi | A61B 1/00006 |
| 11,471,030 | B2* | 10/2022 | Okita | A61B 1/128 |
| 11,596,294 | B2* | 3/2023 | Kitanaka | A61B 1/0058 |
| 11,805,986 | B2* | 11/2023 | Nakamura | A61B 1/0051 |
| 11,839,358 | B2* | 12/2023 | Kugo | A61L 29/02 |
| 2020/0367724 | A1* | 11/2020 | Takahashi | A61B 1/00006 |
| 2021/0000329 | A1* | 1/2021 | Tezuka | A61B 1/00006 |
| 2021/0085156 | A1* | 3/2021 | Kugo | A61B 1/0051 |

FOREIGN PATENT DOCUMENTS

| | | |
|---|---|---|
| JP | 2012-050557 A | 3/2012 |
| JP | 2012-055568 A | 3/2012 |
| JP | 2014-176661 A | 9/2014 |
| WO | 2014/010207 A1 | 1/2014 |
| WO | 2016/121036 A1 | 8/2016 |
| WO | 2016/194200 A1 | 12/2016 |
| WO | 2017/191686 A1 | 11/2017 |
| WO | 2018/189888 A1 | 10/2018 |

OTHER PUBLICATIONS

International Search Report dated Apr. 23, 2019 received in PCT/JP2019/007684.

* cited by examiner

VARIABLE-RIGIDITY DEVICE, CONTROL DEVICE, AND METHOD FOR CONTROLLING ACTUATOR

CROSS REFERENCE TO RELATED APPLICATION

This application is a continuation application of PCT/JP2019/007684 filed on Feb. 27, 2019, the entire contents of which are incorporated herein by this reference.

BACKGROUND OF THE INVENTION

1. Field of the Invention

The present invention relates to a variable-rigidity device that produces a change in rigidity through relative movement of a core member and a tubular member arranged on an outer periphery of the core member in a longitudinal direction, a control device, and a method for controlling an actuator.

2. Description of the Related Art

For observing or treating an inside of an insertion target, such as a living organism or a structure, an insertion device including a flexible insertion portion, which is adapted to be inserted into the insertion target, is used in a medical field and an industrial field, for example. The insertion device includes an endoscope.

For example, International Publication No. WO2017/191686 discloses a variable-rigidity device that changes resistance to bending deformation (i.e., rigidity) of an insertion portion of an insertion device. The variable-rigidity device disclosed in International Publication No. WO2017/191686 includes a core member and a tubular member arranged on an outer periphery of the core member, and can change rigidity of each of the tubular member and the core member by changing the relative positions of the tubular member and the core member in a longitudinal direction.

SUMMARY OF THE INVENTION

A variable-rigidity device according to an aspect of the present invention includes a tubular member including a plurality of high-rigidity portions and low-rigidity portions arranged along a longitudinal axis; a core member arranged on an inner side of the tubular member and including a plurality of high-rigidity core portions and low-rigidity core portions; and an actuator configured to relatively move the core member with respect to the tubular member, in which the actuator is configured to cause a first force to repeatedly fluctuate with a passage of time, the first force causing the core member to relatively move with respect to the tubular member in an axial direction along the longitudinal axis.

A control device according to an aspect of the present invention includes a processor including at least one piece of hardware, in which the processor is configured to, when driving an actuator configured to relatively move a core member with respect to a tubular member in a direction of a longitudinal axis, the core member being arranged on an inner side of the tubular member and including a plurality of high-rigidity core portions and low-rigidity core portions, the tubular member including a plurality of high-rigidity portions and low-rigidity portions arranged along the longitudinal axis, cause a first force to repeatedly fluctuate with a passage of time, the first force causing the core member to relatively move with respect to the tubular member in an axial direction along the longitudinal axis.

A method for controlling an actuator according to an aspect of the present invention includes detecting a load of an actuator when driving the actuator, the actuator being configured to relatively move a core member with respect to a tubular member in a direction of a longitudinal axis, the core member being arranged on an inner side of the tubular member and including a plurality of high-rigidity core portions and low-rigidity core portions, the tubular member including a plurality of high-rigidity portions and low-rigidity portions arranged along the longitudinal axis; when the load is greater than a predetermined threshold, causing a first force to repeatedly fluctuate with a passage of time, the first force causing the core member to relatively move with respect to the tubular member in an axial direction along the longitudinal axis; and when the load is not greater than the predetermined threshold, moving the core member at a predetermined constant speed with respect to the passage of time.

DETAILED DESCRIPTION OF THE PREFERRED EMBODIMENTS

Figure 1:
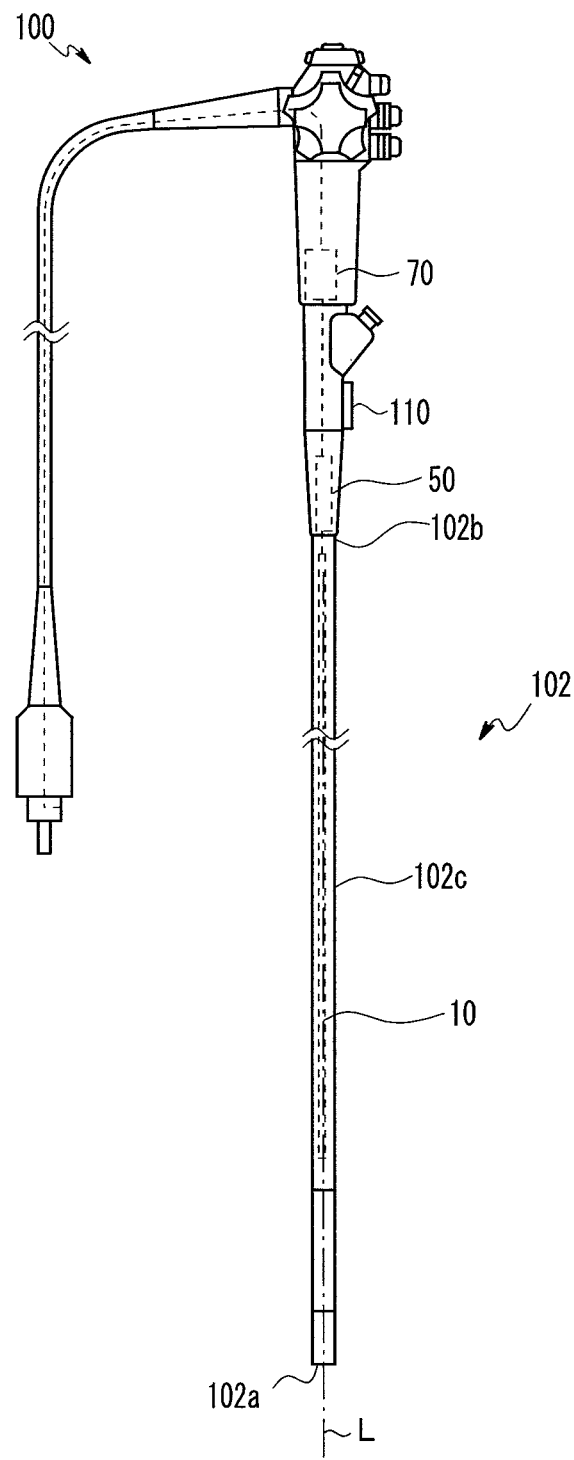
FIG. 1 is a view illustrating the configuration of an insertion device of a first embodiment.

Hereinafter, preferred embodiments of the present invention will be described with reference to the drawings. Note that each component in the drawings used in the following description is illustrated in different scales so as to be perceived on the drawings, and the present invention is not limited to the number of components, the shapes of the components, proportions of the sizes of the components, or the relative positional relationship between the components illustrated in the drawings.

First Embodiment

An insertion device 100 of a first embodiment illustrated in FIG. 1 includes an elongated insertion portion 102 insertable into an insertion target, such as a human body. The insertion portion 102 has a configuration for observing the inside of the insertion target. In other words, in the present embodiment, the insertion device 100 is an endoscope, for example. The insertion target into which the insertion portion 102 of the insertion device 100, which is an endoscope, is inserted, is not limited to a human body, and may be other living organisms or artificial objects, such as machines or building structures. The form of the insertion device 100 is not limited to an endoscope, and may be a treatment instrument for performing medical treatment in a human body, for example.

The insertion portion 102 has an elongated shape. In the following description, an axis lying along the longitudinal direction of the elongated insertion portion 102 is referred to as a longitudinal axis L. The insertion portion 102 includes a flexible tube portion 102c having flexibility. The flexible tube portion 102c may include a so-called bending portion that actively deforms by bending in response to an operation of a user of the insertion device 100. Although the longitudinal axis L illustrated in FIG. 1 is straight, the longitudinal axis L deforms in response to bending deformation of the insertion portion 102.

In the following description, an end of the insertion portion 102 on the side inserted into an insertion target is indicated by a distal end 102a, and an end opposite to the distal end 102a is indicated by a proximal end 102b. In other words, the insertion portion 102 is inserted into an insertion target from the side of the distal end 102a. In addition, a direction along the longitudinal axis L is referred to as an axial direction.

The insertion device 100 includes a variable-rigidity device 10 and an operation portion 110. As described below, the variable-rigidity device 10 is partially arranged in the flexible tube portion 102c of the insertion portion 102. The operation portion 110 is configured to receive an instruction from the user of the insertion device 100 to control the operation of the variable-rigidity device 10. The operation portion 110 includes a switch 11 for the user to operate with his/her finger or foot, for example. The operation portion 110 is electrically connected to a control unit 70 of the variable-rigidity device 10.

Electric power for operating the variable-rigidity device 10 is supplied from an external device to which the insertion device 100 is connected. Examples of the external device include a video processor and a light source device. Note that the insertion device 100 may include a battery that supplies electric power for operating the variable-rigidity device 10. Note also that the operation portion 110 may be partially or entirely provided in an external device to which the insertion device 100 is connected.

Figure 2:
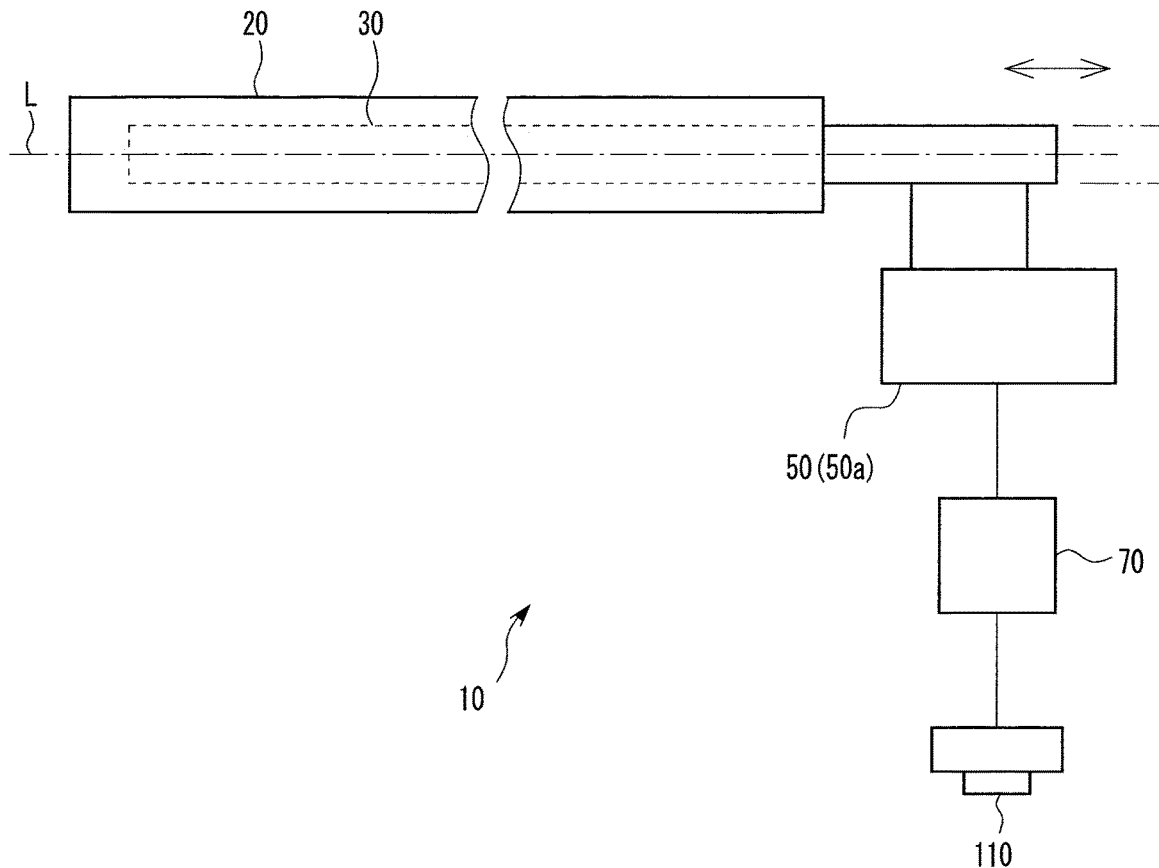
FIG. 2 is a view illustrating the configuration of a variable-rigidity device of the first embodiment.
Figure 3:
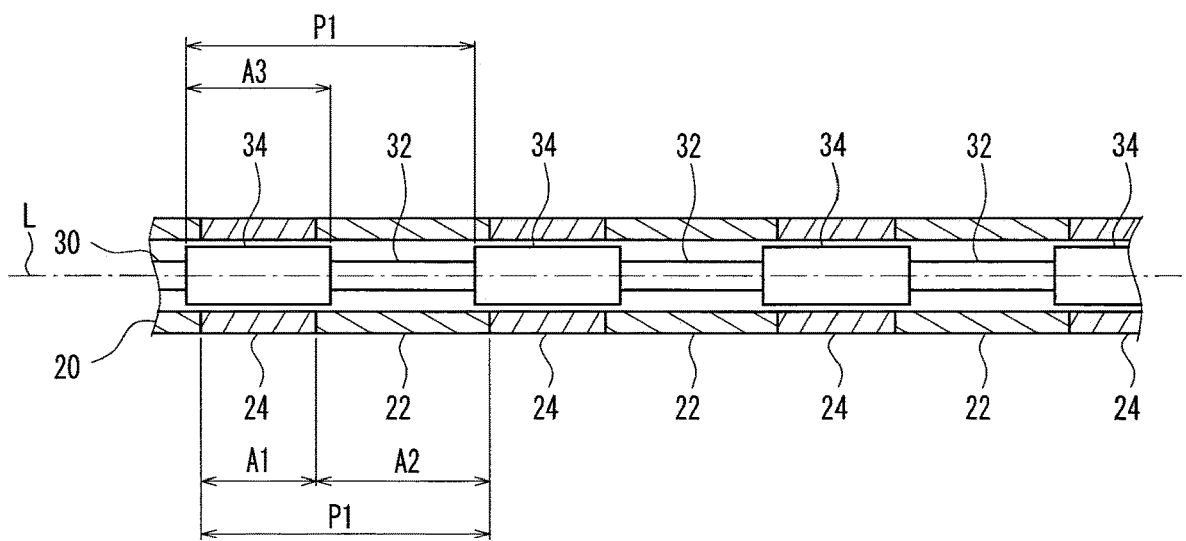
FIG. 3 is a cross-sectional view when a tubular member and a core member of the first embodiment are located at a first position.

FIG. 2 is a view illustrating the configuration of the variable-rigidity device 10. FIG. 3 is a cross-sectional view of the variable-rigidity device 10. As illustrated in FIG. 2, the variable-rigidity device 10 includes a tubular member 20, a core member 30, a drive device 50, and the control unit 70.

The tubular member 20 is arranged extending along the longitudinal axis L in at least a part of the flexible tube portion 102c of the insertion portion 102. The tubular member 20 is a tube-like member with a through-hole provided along the longitudinal axis L.

The tubular member 20 includes, as illustrated in FIG. 3, a plurality of high-rigidity tube portions 22 and one or more low-rigidity tube portions 24. The plurality of high-rigidity tube portions 22 are provided apart from each other along the longitudinal axis L. The low-rigidity tube portion 24 is arranged between the adjacent high-rigidity tube portions 22.

The low-rigidity tube portions 24 have lower flexural rigidity than the high-rigidity tube portions 22. Herein, "flexural rigidity" refers to resistance to bending deformation (i.e., deformation in the bending direction) of the longitudinal axis L. In other words, "flexural rigidity" refers to resistance to deformation for bending the longitudinal axis. Rigidity is represented by a force that is required to bend a section with a predetermined length in a direction along the longitudinal axis L by a predetermined curvature. The higher the rigidity, the less likely it is for the longitudinal axis L to deform in the bending direction.

The plurality of high-rigidity tube portions 22 may have the same level of rigidity or different levels of rigidity. In addition, when more than one low-rigidity tube portion 24 is provided, the low-rigidity tube portions 24 may have the same level of rigidity or different levels of rigidity.

The high-rigidity tube portions 22 and the low-rigidity tube portions 24 are coupled. In the present embodiment illustrated in the drawings, the tubular member 20 includes a plurality of high-rigidity tube portions 22 and a plurality of low-rigidity tube portions 24. The high-rigidity tube portions 22 and the low-rigidity tube portions 24 of the tubular member 20 are alternately arranged along the longitudinal axis L.

Note that in the tubular member 20, the configurations of the high-rigidity tube portions 22 and the low-rigidity tube portions 24 are not limited to particular configurations. In the cross-sectional view illustrated in FIG. 3, each of the high-rigidity tube portions 22 and the low-rigidity tube portions 24 appears to be a single member. However, each of the high-rigidity tube portions 22 and the low-rigidity tube portions 24 may be a combination of a plurality of members.

In addition, in the cross-sectional view illustrated in FIG. 3, the high-rigidity tube portions 22 and the low-rigidity tube portions 24 appear to be different members. However, the high-rigidity tube portions 22 and the low-rigidity tube portions 24 may at least partially include a common member. For example, varying the thickness of a single flexible tubular member can provide the tubular member with the high-rigidity tube portions 22 and the low-rigidity tube portions 24. Alternatively, for example, providing a slit in a part of a single flexible tubular member can provide the tubular member with the high-rigidity tube portions 22 and the low-rigidity tube portions 24.

The core member 30 is partially or entirely arranged on the inner side of the tubular member 20. The core member 30 is relatively movable with respect to the tubular member 20. The core member 30 includes one or more high-rigidity core portions 34 and one or more low-rigidity core portions 32. The high-rigidity core portions 34 and the low-rigidity core portions 32 are connected on the inner side of the tubular member 20.

The low-rigidity core portions 32 have lower flexural rigidity than the high-rigidity core portions 34. When more than one low-rigidity core portion 32 is provided, the low-rigidity core portions 32 may have the same level of rigidity or different levels of rigidity. In addition, when more than one high-rigidity core portion 34 is provided, the high-rigidity core portions 34 may have the same level of rigidity or different levels of rigidity.

In the present embodiment illustrated in the drawings, the core member 30 includes a plurality of high-rigidity core portions 34 and a plurality of low-rigidity core portions 32.

The high-rigidity core portions 34 and the low-rigidity core portions 32 of the core member 30 are alternately arranged along the longitudinal axis L.

Note that in the core member 30, the configurations of the high-rigidity core portions 34 and the low-rigidity core portions 32 are not limited to particular configurations. In the cross-sectional view illustrated in FIG. 3, each of the high-rigidity core portions 34 and the low-rigidity core portions 32 appears to be a single member. However, each of the high-rigidity core portions 34 and the low-rigidity core portions 32 may be a combination of a plurality of members.

In addition, in the cross-sectional view illustrated in FIG. 3, the high-rigidity core portions 34 and the low-rigidity core portions 32 appear to be different members. However, the high-rigidity core portions 34 and the low-rigidity core portions 32 may at least partially include a common member. For example, varying the outside diameter of a single flexible linear member can provide the linear member with the high-rigidity core portions 34 and the low-rigidity core portions 32. Alternatively, for example, providing a slit in a part of a single flexible linear member can provide the linear member with the high-rigidity core portions 34 and the low-rigidity core portions 32.

In the present embodiment, as an example, the tubular member 20 includes a plurality of low-rigidity tube portions 24 each having a length of A1 in a direction along the longitudinal axis L. The plurality of low-rigidity tube portions 24 are arranged in the direction along the longitudinal axis L at a constant pitch P1. In other words, the tubular member 20 includes a plurality of high-rigidity tube portions 22 each having a length of A2 in the direction along the longitudinal axis L. The sum of the length A1 of each low-rigidity tube portion 24 and the length A2 of each high-rigidity tube portion 22 corresponds to the pitch P1.

In addition, in the present embodiment, as an example, the core member 30 includes a plurality of high-rigidity core portions 34 each having a length of A3 in the direction along the longitudinal axis L. The length A3 of each of the plurality of high-rigidity core portions 34 is longer than the length A1 of each low-rigidity tube portion 24. The plurality of high-rigidity core portions 34 are arranged in the direction along the longitudinal axis L at the constant pitch P1.

Figure 4:
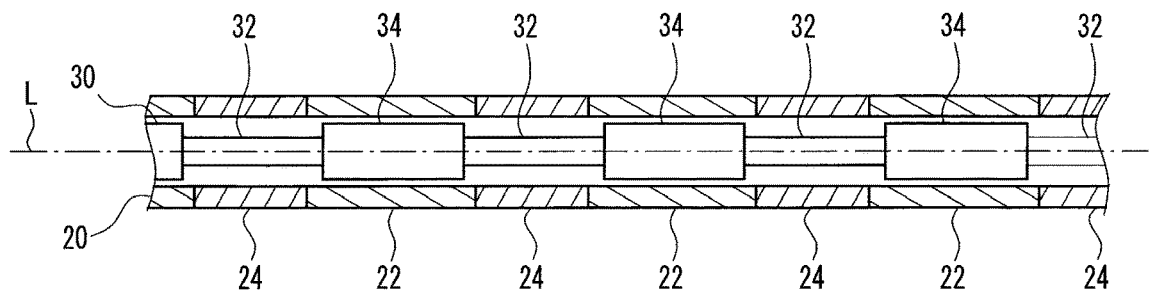
FIG. 4 is a cross-sectional view when the tubular member and the core member of the first embodiment are located at a second position.

As illustrated in FIGS. 3 and 4, in the variable-rigidity device 10 of the present embodiment, the core member 30 can be relatively moved with respect to the tubular member 20 in the direction along the longitudinal axis L through a predetermined operation of the drive device 50 described below. As illustrated in FIG. 3, w % ben the center of each high-rigidity core portion 34 is located at substantially the same position as the center of each low-rigidity tube portion 24 in the direction along the longitudinal axis L, the rigidity of each of the tubular member 20 and the core member 30 is high. On the other hand, as illustrated in FIG. 4, when the center of each high-rigidity core portion 34 is located at substantially the same position as the center of each high-rigidity tube portion 22 in the direction along the longitudinal axis L, the rigidity of each of the tubular member 20 and the core member 30 is low.

In the following description, a state in which the core member 30 and the tubular member 20 have a positional relationship such that the center of each high-rigidity core portion 34 is substantially the same as the center of each low-rigidity tube portion 24 as illustrated in FIG. 3 is referred to as a first position. In addition, a state in which the core member 30 and the tubular member 20 have a positional relationship such that the center of each high-rigidity core portion 34 is substantially the same as the center of each high-rigidity tube portion 22 as illustrated in FIG. 4 is referred to as a second position.

The drive device 50 is a device configured to move the core member 30 and the tubular member 20 between the first position and the second position. The drive device 50 is connected to at least one of the tubular member 20 or the core member 30, and is configured to relatively move the core member 30 with respect to the tubular member 20.

The drive device 50 executes one or both of a first operation of generating a first force for relatively moving the core member 30 with respect to the tubular member 20 in the axial direction along the longitudinal axis L while causing at least one of the strength or direction of the first force to fluctuate with a passage of time, and a second operation of generating the first force and also generating a second force for relatively moving the core member 30 with respect to the tubular member 20 in a rotation direction about the longitudinal axis L while causing at least one of the strength or direction of the second force to fluctuate with a passage of time.

In the present embodiment, as an example, the drive device 50 executes only the first operation. Specifically, the drive device 50 of the present embodiment includes one actuator 50*a* configured to generate the first force. The actuator 50*a* includes an electric motor, for example.

The control unit 70 is electrically connected to the drive device 50. The control unit 70 includes a processor and a storage unit configured to store a predetermined program, and also includes hardware configured to control the operation of the drive device 50 based on the program.

Figure 5:
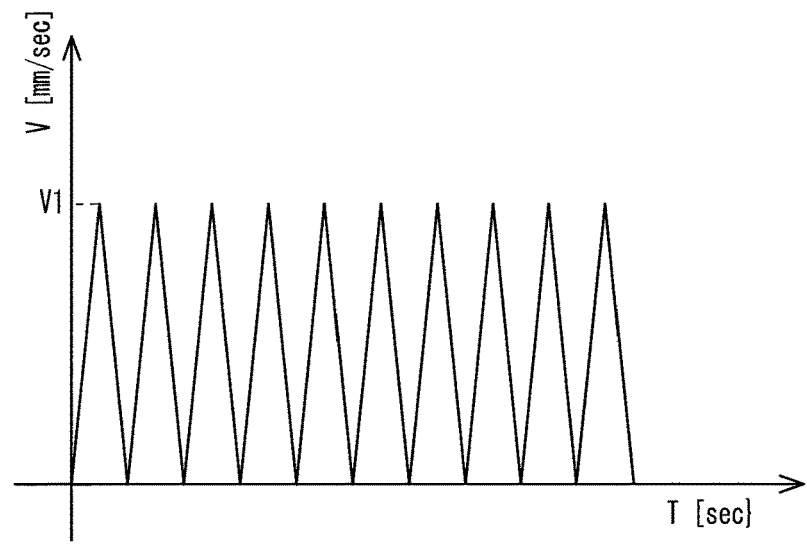
FIG. 5 is a graph illustrating a first operation of a drive device of the first embodiment.

The drive device 50 executes the first operation under the control of the control unit 70. FIG. 5 is a graph illustrating a method for controlling the drive device 50 during execution of the first operation. In the graph of FIG. 5, a horizontal axis indicates a time T. and a vertical axis indicates a command speed V. The command speed V is a target relative speed of the core member 30 with respect to the tubular member 20 in the axial direction.

As illustrated in FIG. 5, the control unit 70 causes the command speed V to repeatedly fluctuate in a triangular wave pattern when the first operation of the drive device 50 is executed. In other words, the drive device 50 of the present embodiment causes the strength of the first force to fluctuate with a passage of time during execution of the first operation. The drive device 50 repeatedly applies an impact load to at least one of the core member 30 or the tubular member 20 through execution of the first operation.

When the switch 111 of the operation portion 110 is on, the control unit 70 determines that a hardening instruction for increasing the rigidity of the variable-rigidity device 10 is inputted.

When the control unit 70 determines that a hardening instruction is inputted in a state in which the hardening instruction has not been inputted, the control unit 70 causes the drive device 50 to execute the first operation, and executes a hardening control process of moving the relative position of the core member 30 with respect to the tubular member 20 from the second position to the first position. In addition, when the control unit 70 determines that a hardening instruction is no longer inputted in a state in which the hardening instruction has been inputted, the control unit 70 causes the drive device 50 to execute the first operation, and executes a softening control process of moving the relative position of the core member 30 with respect to the tubular member 20 from the first position to the second position.

When the hardening control process is complete, the relative position of the core member 30 with respect to the tubular member 20 is at the first position. Thus, the rigidity of each of the core member 30 and the tubular member 20 is high (FIG. 3). Therefore, the execution of the hardening control process allows the flexible tube portion 102c of the insertion device 100 to have high rigidity. In addition, when the softening control process is complete, the relative position of the core member 30 with respect to the tubular member 20 is at the second position. Thus, the rigidity of each of the core member 30 and the tubular member 20 is low (FIG. 4). Therefore, the execution of the softening control process allows the flexible tube portion 102c of the insertion device 100 to have low rigidity. In this manner, the variable-rigidity device 10 of the present embodiment can change the rigidity of the flexible tube portion 102c of the insertion device 100.

For example, a frictional force between the core member 30 and the tubular member 20 in a state in which the flexible tube portion 102c of the insertion device 100 is bent and the core member 30 and the tubular member 20 are bent is higher than when the core member 30 and the tubular member 20 are straight.

In the variable-rigidity device 10 of the present embodiment, to relatively move the core member 30 with respect to the tubular member 20 in the axial direction, the drive device 50 repeatedly generates an impact load in the axial direction. Therefore, even when a frictional force between the core member 30 and the tubular member 20 is high, the relative position of the core member 30 with respect to the tubular member 20 can be immediately moved to a predetermined position. In other words, the variable-rigidity device 10 of the present embodiment is capable of stable operation regardless of changes in a frictional force between the core member 30 and the tubular member 20.

Figure 6:
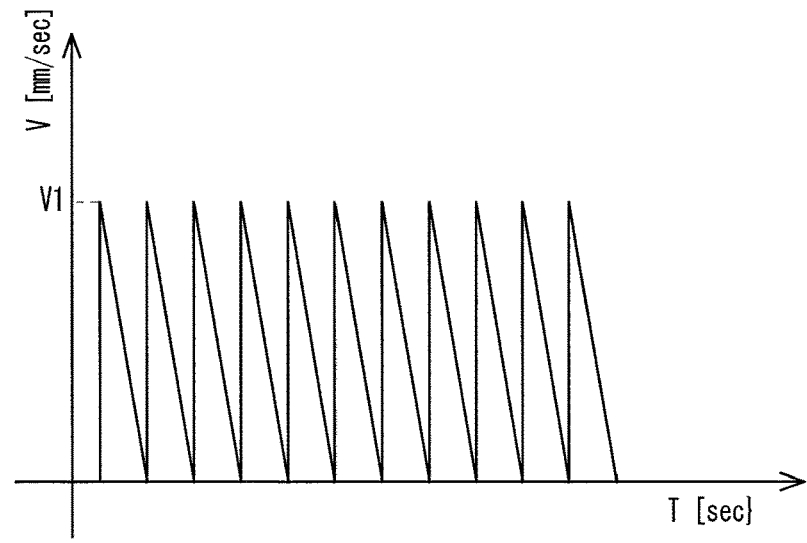
FIG. 6 is a graph illustrating a first modification of the first operation of the drive device of the first embodiment.

Note that the command speed V issued when the drive device 50 executes the first operation may be in a sawtooth waveform pattern as in a first modification illustrated in FIG. 6. In the first modification illustrated in FIG. 6, the inclination of the speed on the side increasing with a passage of time is greater than the inclination of the speed on the side decreasing with a passage of time.

Figure 7:
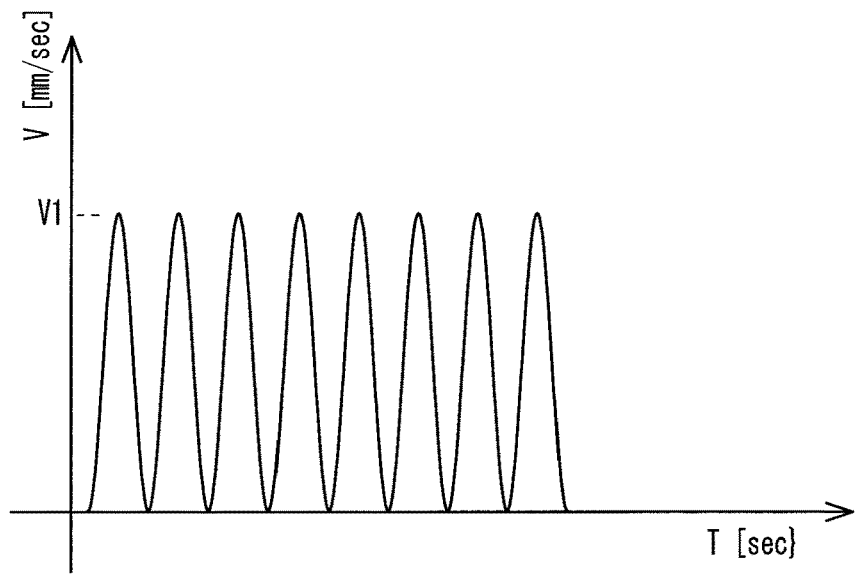
FIG. 7 is a graph illustrating a second modification of the first operation of the drive device of the first embodiment.
Figure 8:
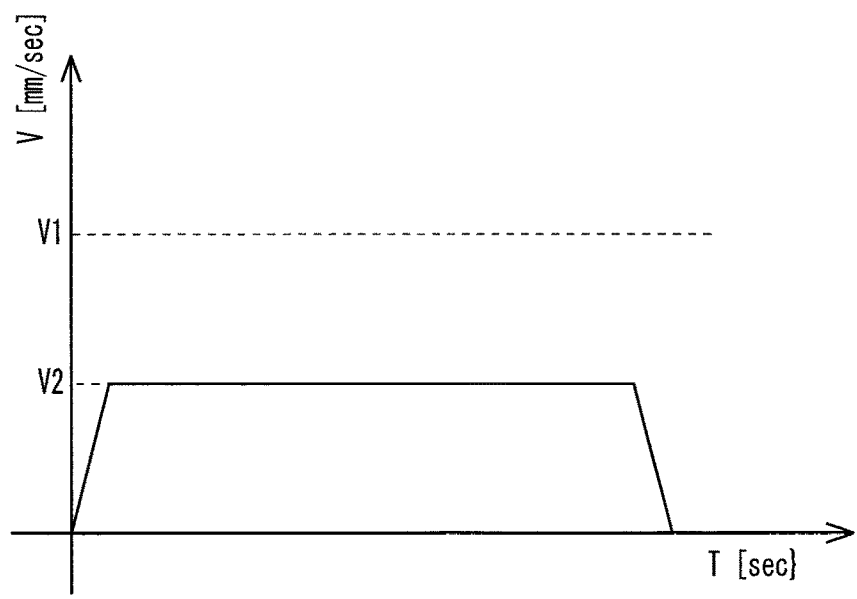
FIG. 8 is a graph illustrating a third operation of a drive device of a second embodiment.

Alternatively, the command speed V issued when the drive device 50 executes the first operation may be in a sine waveform pattern as in a second modification illustrated in FIG. 7. Driving the actuator 50a of the drive device 50 using sine waves can reduce noise generated during operation of the drive device 50.

Second Embodiment

Hereinafter, a second embodiment of the present invention will be described. The following will describe only differences from the first embodiment. Components similar to the components of the first embodiment are denoted by identical reference numerals, and descriptions of such components are omitted as appropriate.

The variable-rigidity device 10 of the present embodiment differs from the variable-rigidity device 10 of the first embodiment in the operations of the drive device 50 and the control unit 70.

The drive device 50 of the present embodiment can execute a third operation in addition to the first operation. In the third operation, the drive device 50 generates a first force to relatively move the core member 30 with respect to the tubular member 20 in the axial direction at a predetermined constant speed V2. The speed V2 is lower than a peak speed V1 of the first operation.

Figure 9:
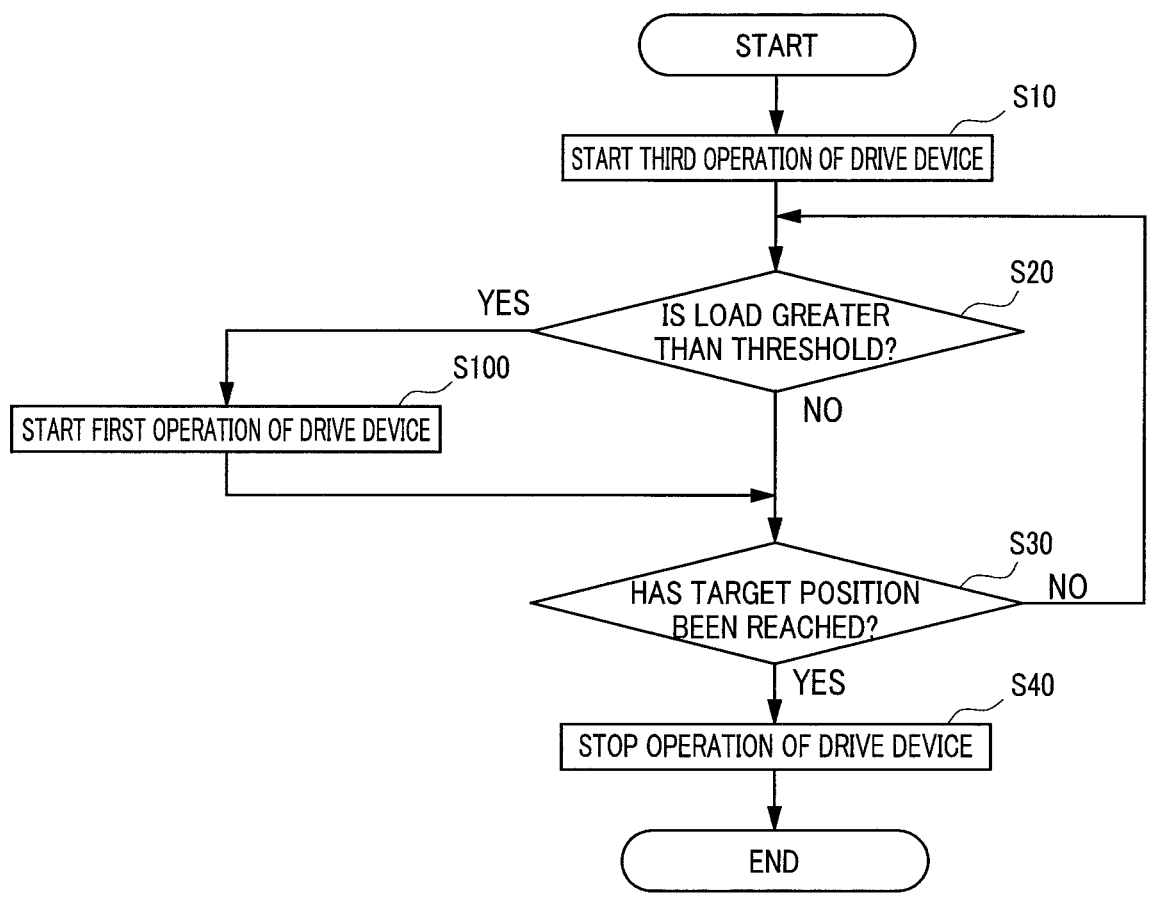
FIG. 9 is a flowchart of a hardening control process of the second embodiment.

FIG. 9 illustrates a flowchart of a hardening control process executed by the control unit 70. In the hardening control process, first, in step S10, the control unit 70 starts execution of the third operation with the drive device 50. Herein, the direction of a force generated by the drive device 50 is a direction for moving the relative position of the core member 30 with respect to the tubular member 20 from the second position to the first position. As described previously, in the third operation, the command speed V has a constant value V2.

Next, in step S20, the control unit 70 determines if a load of the actuator 50a has exceeded a threshold. The method of detecting the load of the actuator 50a with the control unit 70 is not limited to a particular method. In the present embodiment, as an example, the control unit 70 detects the load based on a current value of the actuator 50a. The control unit 70 determines that the load of the actuator 50a has exceeded the threshold when the current value of the actuator 50a has exceeded a predetermined value. Note that the load of the actuator 50a can also be detected with a strain sensor, a pressure sensor, or a torque sensor, for example.

In the determination of step S20, if the load of the actuator 50a is less than or equal to the threshold, the control unit 70 proceeds to step S30. In step S30, the control unit 70 determines if the relative position of the core member 30 with respect to the tubular member 20 has reached the first position as a target position.

In step S30, if the control unit 70 determines that the relative position of the core member 30 with respect to the tubular member 20 has reached the first position, the control unit 70 proceeds to step S40 to stop the operation of the drive device 50, and terminates the hardening control process.

On the other hand, in step S30, if the control unit 70 determines that the relative position of the core member 30 with respect to the tubular member 20 has not reached the first position, the control unit 70 returns to step S20.

In the determination of step S20, if the load of the actuator 50a is greater than the threshold, the control unit 70 proceeds to step S100. In step S100, the control unit 70 starts execution of the first operation with the drive device 50. Herein, the direction of a force generated by the drive device 50 is a direction for moving the relative position of the core member 30 with respect to the tubular member 20 from the second position to the first position. As described in the first embodiment, through the execution of the first operation, the drive device 50 repeatedly applies an impact load to at least one of the core member 30 or the tubular member 20.

Note that the command speed V outputted to the drive device 50 from the control unit 70 during the execution of step S100 may be a speed obtained by adding the speed V2 to the repetitive triangular waves illustrated in FIG. 5. In other words, during the execution of step S100, the drive device 50 may concurrently execute the first operation and the third operation.

After the execution of step S100, the control unit 70 proceeds to step S30. When the hardening control process is complete, the relative position of the core member 30 with respect to the tubular member 20 is at the first position. Therefore, the rigidity of each of the core member 30 and the tubular member 20 is high (FIG. 3).

As described above, in the hardening control process of the present embodiment, if the control unit 70 detects that the load of the actuator 50a has exceeded a threshold while the drive device 50 is executing the third operation, the first operation is executed. In the softening control process, if the control unit 70 detects that the load of the actuator 50a has exceeded a threshold while the drive device 50 is executing the third operation, the first operation is executed as in the hardening control process.

The reason that the load of the actuator 50a becomes high while the drive device 50 is executing the third operation is that a frictional force between the core member 30 and the tubular member 20 increases. For example, a frictional force between the core member 30 and the tubular member 20 in a state in which the core member 30 and the tubular member 20 are bent is higher than when the core member 30 and the tubular member 20 are straight.

In the variable-rigidity device 10 of the present embodiment, to change the relative position of the core member 30 with respect to the tubular member 20 in a state in which a frictional force between the core member 30 and the tubular member 20 is high, the drive device 50 executes the first operation to repeatedly generate an impact load. Therefore, the relative position of the core member 30 with respect to the tubular member 20 can be immediately moved to a predetermined position. In other words, the variable-rigidity device 10 of the present embodiment is capable of stable operation regardless of changes in a frictional force between the core member 30 and the tubular member 20.

In addition, in the variable-rigidity device 10 of the present embodiment, when a frictional force between the core member 30 and the tubular member 20 is low, the drive device 50 operates at the constant speed V2. Therefore, generation of vibration and noise can be suppressed.

Note that in the present embodiment, the command speed V issued when the drive device 50 executes the first operation may be in a sawtooth waveform pattern as illustrated in FIG. 6 or a sine waveform pattern as illustrated in FIG. 7 as in the first embodiment.

Third Embodiment

Hereinafter, a third embodiment of the present invention will be described. The following will describe only differences from the first embodiment. Components similar to the components of the first embodiment are denoted by identical reference numerals, and descriptions of such components are omitted as appropriate.

Figure 10:
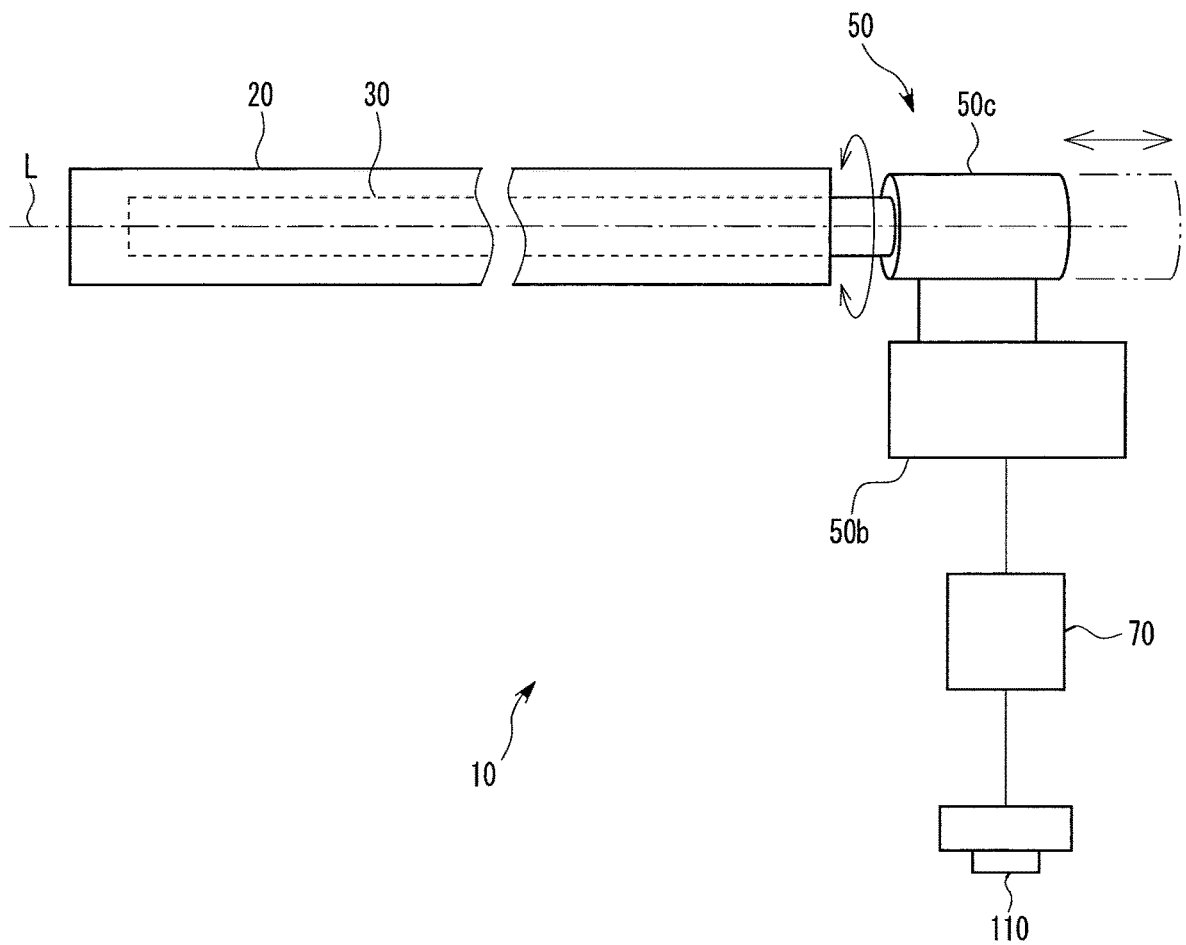
FIG. 10 is a view illustrating the configuration of an insertion device of a third embodiment.

The variable-rigidity device 10 of the present embodiment illustrated in FIG. 10 differs from the variable-rigidity device 10 of the first embodiment in the configuration and operation of the drive device 50.

The drive device 50 of the present embodiment includes a first actuator 50b and a second actuator 50c. The drive device 50 can execute only the second operation.

The first actuator 50b generates a first force for moving the core member 30 with respect to the tubular member 20 in the axial direction. The first actuator 50b includes an electric motor, for example.

The second actuator 50c generates a second force for relatively moving the core member 30 with respect to the tubular member 20 in a rotation direction about the longitudinal axis L. The second actuator 50c includes an electric motor, for example.

During execution of the second operation, the drive device 50 generates the first force with the first actuator 50b, and concurrently generates the second force with the second actuator 50c while causing at least one of the strength or direction of the second force to fluctuate with a passage of time.

Figure 11:
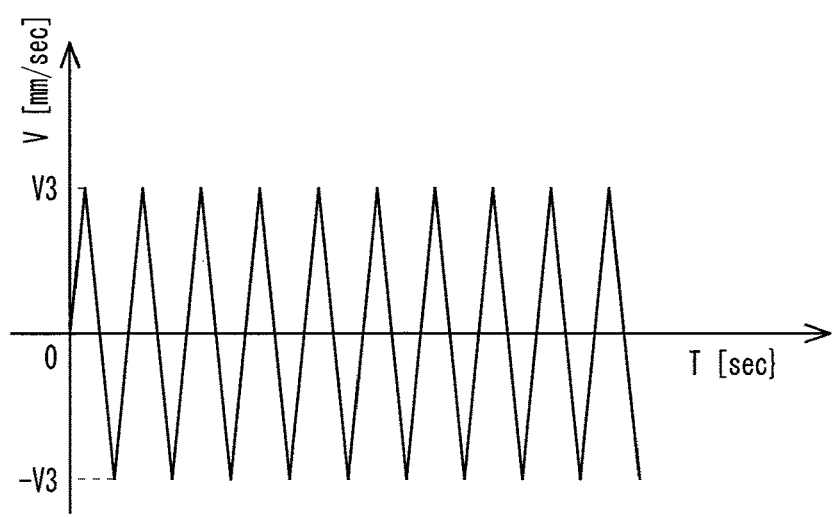
FIG. 11 is a graph illustrating a second operation of a drive device of the third embodiment.

FIG. 11 is a graph illustrating a method for controlling the second actuator 50c during execution of the second operation. A command speed V is a target rotation speed of the core member 30 with respect to the tubular member 20 about a rotation axis. When the command speed V has a positive value, the second actuator 50c rotates in a forward direction, and when the command speed V has a negative value, the second actuator 50c rotates in a reverse direction. Note that the command speed V for the second actuator 50c issued during execution of the second operation may be either in a rectangular waveform pattern or a sine waveform pattern.

As illustrated in FIG. 11, when the control unit 70 executes the second operation of the drive device 50, the control unit 70 causes the command speed V for the second actuator 50c to repeatedly fluctuate in a triangular wave pattern and also repeatedly reverses the rotation direction. In other words, while the drive device 50 is executing the second operation, the core member 30 relatively oscillates with respect to the tubular member 20 in the rotation direction about the rotation axis. As in the first embodiment, the control unit 70 executes the second operation of the drive device 50 in a hardening control process and a softening control process.

In the variable-rigidity device 10 of the present embodiment, when the core member 30 is relatively moved with respect to the tubular member 20 in the axial direction, the core member 30 relatively oscillates with respect to the tubular member 20 in the rotation direction about the rotation axis. Therefore, the variable-rigidity device 10 is capable of stable operation regardless of changes in a frictional force between the core member 30 and the tubular member 20.

Fourth Embodiment

Hereinafter, a fourth embodiment of the present invention will be described. The following will describe only differences from the first embodiment. Components similar to the components of the first embodiment are denoted by identical reference numerals, and descriptions of such components are omitted as appropriate.

The variable-rigidity device 10 of the present embodiment differs from the variable-rigidity device 10 of the third embodiment in the operations of the drive device 50 and the control unit 70.

The drive device 50 of the present embodiment can execute a third operation in addition to the second operation. In the third operation, the drive device 50 generates a first force to relatively move the core member 30 with respect to the tubular member 20 in the axial direction at a predetermined constant speed. In other words, during execution of the third operation, the command speed for the first actuator 50b is constant.

Figure 12:
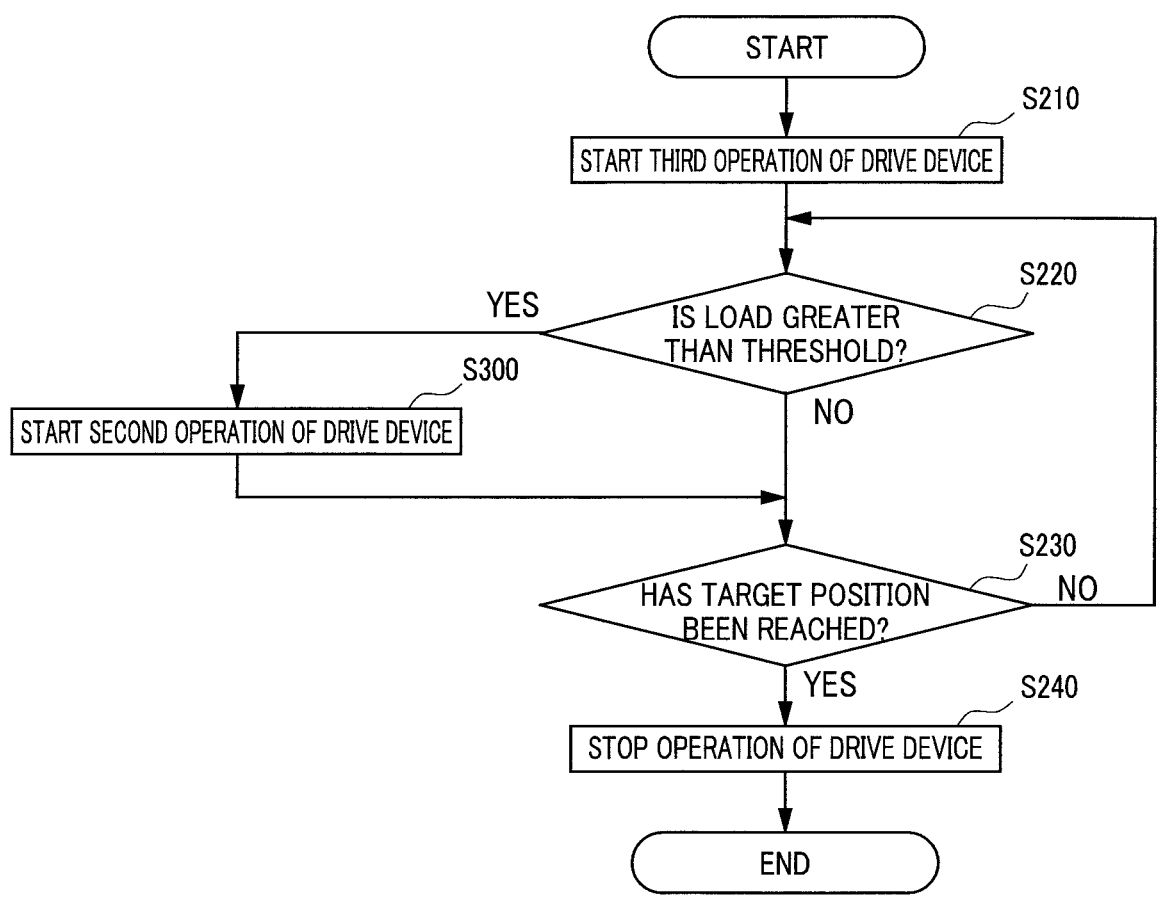
FIG. 12 is a flowchart of a hardening control process of a fourth embodiment.

FIG. 12 illustrates a flowchart of a hardening control process executed by the control unit 70. In the hardening control process, first, in step S210, the control unit 70 starts execution of the third operation with the drive device 50. Herein, the direction of a force generated by the drive device 50 is a direction for moving the relative position of the core member 30 with respect to the tubular member 20 from the second position to the first position. In step S210, the control unit 70 sets the command speed for the first actuator 50b to a constant value.

Next, in step S220, the control unit 70 determines if a load of the first actuator 50b has exceeded a threshold. The method for detecting the load of the first actuator 50b with the control unit 70 is not limited to a particular method. In the present embodiment, as an example, the control unit 70 detects the load based on a current value of the first actuator 50b. The control unit 70 determines that the load of the first actuator 50b has exceeded the threshold when the current value of the first actuator 50b has exceeded a predetermined value. Note that the load of the first actuator 50b can also be detected with a strain sensor, a pressure sensor, or a torque sensor, for example.

In the determination of step S220, if the load of the first actuator 50b is less than or equal to the threshold, the control unit 70 proceeds to step S230. In step S230, the control unit 70 determines if the relative position of the core member 30 with respect to the tubular member 20 has reached the first position as a target position.

In step S230, if the control unit 70 determines that the relative position of the core member 30 with respect to the tubular member 20 has reached the first position, the control unit 70 proceeds to step S240 to stop the operation of the drive device 50, and terminates the hardening control process.

On the other hand, in step S230, if the control unit 70 determines that the relative position of the core member 30 with respect to the tubular member 20 has not reached the first position, the control unit 70 returns to step S220.

In the determination of step S220, if the load of the first actuator 50b is greater than the threshold, the control unit 70 proceeds to step S300. In step S300, the control unit 70 starts execution of the second operation with the drive device 50.

Through the execution of the second operation, the drive device 50 generates a first force for relatively moving the core member 30 with respect to the tubular member 20 in the axial direction, and concurrently generates a second force for causing the core member 30 to relatively oscillate with respect to the tubular member 20 about the rotation axis.

After the execution of step S300, the control unit 70 proceeds to step S230. When the hardening control process is complete, the relative position of the core member 30 with respect to the tubular member 20 is at the first position. Therefore, the rigidity of each of the core member 30 and the tubular member 20 is high (FIG. 3).

As described above, in the hardening control process of the present embodiment, if the control unit 70 detects that the load of the first actuator 50b has exceeded a threshold while the drive device 50 is executing the third operation, the second operation is executed. In the softening control process, if the control unit 70 detects that the load of the first actuator 50b has exceeded a threshold while the drive device 50 is executing the third operation, the second operation is executed as in the hardening control process.

The reason that the load of the first actuator 50b becomes high while the drive device 50 is executing the third operation is that a frictional force between the core member 30 and the tubular member 20 increases. For example, a frictional force between the core member 30 and the tubular member 20 in a state in which the core member 30 and the tubular member 20 are bent is higher than when the core member 30 and the tubular member 20 are straight.

In the variable-rigidity device 10 of the present embodiment, to change the relative position of the core member 30 with respect to the tubular member 20 in a state in which a frictional force between the core member 30 and the tubular member 20 is high, the drive device 50 causes the core member 30 to relatively oscillate with respect to the tubular member 20 about the rotation axis. Therefore, the relative position of the core member 30 with respect to the tubular member 20 can be immediately moved to a predetermined position. In other words, the variable-rigidity device 10 of the present embodiment is capable of stable operation regardless of changes in a frictional force between the core member 30 and the tubular member 20.

In addition, in the variable-rigidity device 10 of the present embodiment, when a frictional force between the core member 30 and the tubular member 20 is low, the first actuator 50b operates. Therefore, generation of vibration and noise can be suppressed.

The present invention is not limited to the aforementioned embodiments, and can be changed as appropriate within the gist and spirit of the invention read from the entire claims and specification. A variable-rigidity device that involves such a change is also encompassed by the technical scope of the present invention.

What is claimed is:

1. A variable-rigidity device comprising:
a tubular member including a plurality of first tube parts and second tube parts arranged along a longitudinal axis, a rigidity of the first tube parts being higher than a rigidity of the second tube parts;
a core member arranged on an inner side of the tubular member and including a plurality of first core parts and second core parts, a rigidity of the first core parts being higher than a rigidity of the second core parts;
an actuator configured to relatively move the core member with respect to the tubular member; and
a controller configured to control the relative movement by the actuator;
wherein the controller is configured to cause a first force to repeatedly fluctuate with a passage of time, the first force causing the core member to relatively move with respect to the tubular member in an axial direction along the longitudinal axis.

2. The variable-rigidity device according to claim 1, wherein a direction in which the first force is applied is caused to fluctuate with the passage of time.

3. The variable-rigidity device according to claim 1, wherein the controller is configured to cause a second force to repeatedly fluctuate with the passage of time, the second force causing the core member to relatively move with respect to the tubular member in a rotation direction about the longitudinal axis.

4. The variable-rigidity device according to claim 3, wherein the rotation direction is repeatedly reversed with the passage of time.

5. The variable-rigidity device according to claim 3, wherein the controller is configured to control the actuator:
to move the core member at a predetermined constant speed with respect to the passage of time when relatively moving the core member with respect to the tubular member in the axial direction along the longitudinal axis, and
to cause the second force to repeatedly fluctuate with the passage of time when the controller detects that a load of the actuator is greater than a threshold during execution of the operation.

6. The variable-rigidity device according to claim 1, wherein the controller is configured to control the actuator:
to move the core member at a predetermined constant speed with respect to the passage of time when relatively moving the core member with respect to the tubular member in the axial direction along the longitudinal axis, and
to cause the first force to repeatedly fluctuate with the passage of time when the controller detects that a load of the actuator is greater than a threshold during execution of the operation.

7. A control device comprising a processor including at least one piece of hardware, wherein the processor is configured to, when driving an actuator configured to relatively move a core member with respect to a tubular member in a direction of a longitudinal axis, the core member being arranged on an inner side of the tubular member and including a plurality of first core parts and second core parts, a rigidity of the first core parts being higher than a rigidity of the second core parts, the tubular member including a plurality of first tube parts and second tube parts arranged along the longitudinal axis, a rigidity of the first tube parts being higher than a rigidity of the second tube parts, cause a first force to repeatedly fluctuate with a passage of time, the first force causing the core member to relatively move with respect to the tubular member in an axial direction along the longitudinal axis.

8. The control device according to claim 7, wherein a direction in which the first force is applied is caused to fluctuate with the passage of time.

9. The control device according to claim 7, wherein the processor is configured to cause a second force to repeatedly fluctuate with h passage of time, the second force causing the core member to relatively move with respect to the tubular member in a rotation direction about the longitudinal axis.

10. The control device according to claim 9, wherein the rotation direction is repeatedly reversed with the passage of time.

11. A method for controlling an actuator, comprising:
detecting a load of h actuator when driving the actuator, the actuator being configured to relatively move a core member with respect to a tubular member in a direction of a longitudinal axis, the core member being arranged on an inner side of the tubular member and including a plurality of first core parts and second core parts, a rigidity of the first core parts being higher than a rigidity of the second core parts, the tubular member including a plurality of first tube parts and second tube parts arranged along the longitudinal axis, a rigidity of the first tube arts being higher than a rigidity of the second tube parts;

when the load is greater than a predetermined threshold, causing a first force to repeatedly fluctuate with a passage of time, the first force causing the core member to relatively move with respect to the tubular member in an axial direction along the longitudinal axis; and when the load is not greater than the predetermined threshold, moving the core member at a predetermined constant speed with respect to the passage of time.

* * * * *